(12) United States Patent
Corr et al.

(10) Patent No.: US 7,567,371 B2
(45) Date of Patent: Jul. 28, 2009

(54) ELECTROCHROMIC COMPOUNDS

(75) Inventors: David Corr, Goatstown (IE); S. N. Rao, Dublin (IE); Niall Stobie, Coolock (IE); Mark Kinsella, Oldtown (IE)

(73) Assignee: Ntera Limited, Dublin (IE)

( * ) Notice: Subject to any disclaimer, the term of this patent is extended or adjusted under 35 U.S.C. 154(b) by 385 days.

(21) Appl. No.: 10/543,588

(22) PCT Filed: Jan. 30, 2004

(86) PCT No.: PCT/IE2004/000015

§ 371 (c)(1),
(2), (4) Date: Nov. 2, 2005

(87) PCT Pub. No.: WO2004/067673

PCT Pub. Date: Aug. 12, 2004

(65) Prior Publication Data

US 2006/0110638 A1    May 25, 2006

(30) Foreign Application Priority Data

Jan. 31, 2003   (EP)  .................. 03394012

(51) Int. Cl.
$G02F\ 1/15$   (2006.01)
(52) U.S. Cl. ..................... 359/273; 359/265
(58) Field of Classification Search ............ 359/265, 359/275
See application file for complete search history.

(56) References Cited

U.S. PATENT DOCUMENTS 5,695,890 A   12/1997   Thompson et al.

2002/0021482 A1 *   2/2002   Fitzmaurice et al. ........ 359/265

FOREIGN PATENT DOCUMENTS

EP   1 271 227 A1   1/2003
WO   99/03154 A1    1/1999

OTHER PUBLICATIONS

XP-002247699: Rao, S.N, et al., "Heterosupramolecular Chemistry: Synthetic Strategies For The Covalent And Noncovalent Assembly And Organization Of Nanocrystals And Molecules", *Helvetica Chimica Acta*, vol. 81, No. 5, pp. 902-915, (1998).
XP-004157010: Cinnsealach, R., et al., "Coloured Electrochromic Windows Based On Nanostructured $TiO_2$ Films Modified By Adsorbed Redox Chromophores" *Solar Energy Materials & Solar Cells*, vol. 57, No. 2, pp. 107-125, (1999).
XP-004154415: Campus, F., et al., "Electrochromic Devices Based On Surface-modified Nanocrystalline $TiO_2$ Thin-film Electrodes", *Solar Energy Materials & Solar Cells*, vol. 56, No. 3-4, pp. 281-297, (1999).
XP-004154421: Coleman, J.P., et al., "Printed, Flexible Electrochromic Displays Using Interdigitated Electrodes", *Solar Energy Materials & Solar Cells*, vol. 56, No. 3-4, pp. 395-418, (1999).

* cited by examiner

*Primary Examiner*—Joseph Martinez
(74) *Attorney, Agent, or Firm*—Morgan, Lewis & Bockius LLP

(57) ABSTRACT

The invention concerns electrochromic compounds of the general formula I. These compounds may be used in electrochromic devices, especially electrochromic devices comprising nanostructured films.

2 Claims, No Drawings

ELECTROCHROMIC COMPOUNDS

This invention relates to novel electrochromic compounds. These compounds are useful in electrochromic devices such as electric windows, displays and other optical devices that can change colour according to the needs of the user. In particular, the compounds may be used in electrochromic devices comprising nanostructured films.

Viologen compounds, i.e. compounds which have a dipyridinium group and are capable of reversible reduction/colouration, are widely used in electrochromic devices. However, in conventional viologen-based systems, diners may be formed due to the parallel overlap of viologens, thereby preventing efficient decolouration in the electrochromic device.

It is an object of the invention to avoid or minimise the disadvantages of the prior art.

According to the present invention there are provided compounds of the general formula I

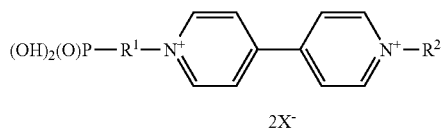

$R^1$ is —$(CH_2)_m$— wherein m is zero or an integer from 1 to 10; or aryl or heteroaryl having up to 14 carbon atoms; or branched-chain alkyl or alkenyl, or cycloalkyl, each having up to 10 carbon atoms; the aryl, heteroaryl, branched alkyl, branched alkenyl or cycloalkyl radical optionally being attached to the —$P(O)(OH)_2$ group via a —$(CH_2)_n$— linkage, wherein n is zero or an integer from 1 to 10; it also being possible for the aryl, heteroaryl, branched alkyl, branched alkenyl or cycloalkyl radical to be optionally substituted by one or more of the following substituents which may be the same or different: lower alkyl, lower alkenyl, phenyl-lower alkyl, diphenyl-lower alkyl, phenyl, phenoxy, lower alkanoyloxy, halogen, amino, cyano, nitro, lower alkylamino, di-lower alkylamino, phenylamino, lower alkanoylamino, benzoylamino; lower alkylsulfonylamino, phenysulfonylamino, lower alkanoyl, benzoyl, carboxy, lower alkoxycarbonyl, carbamoyl, N-lower alkylcarbamoyl, N,N-di-lower alkylcarbamoyl, ureido, N-lower alkylureido, lower alkylsulfonyl; phenylsulfonyl; lower alkyl which is substituted by hydroxy, lower alkoxy, amino, lower alkylamino, di-lower alkylamino, halogen, carboxy or lower alkoxycarbonyl; lower alkoxy which is substituted by hydroxy, lower alkoxy, amino, lower alkylamino, di-lower alkylamino, halogen, carboxy or lower alkoxycarbonyl; $C_3$-$C_7$-alkoxy; and/or bivalent methylenedioxy; it being possible for all phenyl groups mentioned as such or in composed radicals (such as benzoyl, phenylamino etc.) to be unsubstituted or substituted by lower alkyl, lower alkoxy, halogen, hydroxy and/or nitro; and $R^2$ is $R^3R^4$ wherein $R^3$ is —$(CH_2)_p$— wherein p is zero or an integer from 1 to 10; and $R^4$ is —$P(O)(OH)_2$; or aryl or heteroaryl having up to 14 carbon atoms; or branched-chain alkyl or alkenyl, or cycloalkyl, each having up to 10 carbon atoms, it being possible for the aryl, heteroaryl, branched alkyl, branched alkenyl or cycloalkyl radical to be unsubstituted or substituted by one or more of the substituents given in the definition of $R^1$; and $X^-$ is a charge-balancing ion;

with the provisos that $R^1$ cannot be —$(CH_2)_m$— wherein m is 2 or 3, when $R^2$ is —$(CH_2)_2$—$P(O)(OH)_2$; and $R^1$ cannot be —$(CH_2)_m$— wherein m is 2, when $R^2$ is phenyl.

The invention also provides processes for the manufacture of the compounds of formula I, electrochromic devices comprising said compounds, and their use in the manufacture of electrochromic devices.

The invention further provides intermediate compounds which are useful in the preparation of the compounds of formula I, said intermediate compounds having the general formula V

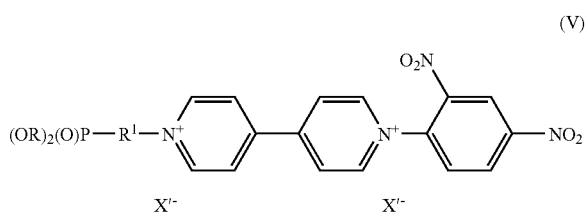

wherein $R^1$ is as defined in formula I except that the provisos are excluded, each R is an ester forming group which may be the same or different, and each $X'^-$ is independently halogen. The compounds of formula V have electrochromic properties and may be used in electrochromic devices.

The general definitions used herein have the following meanings within the scope of the present invention.

The term "lower" means that groups so defined have preferably up to and including 7, especially up to and including 4, carbon atoms.

Lower alkyl as such or in composed radicals such as lower alkoxy etc. is e.g. n-propyl, isopropyl, n-butyl, isobutyl, sec.-butyl, tert.-butyl, n-pentyl, isopentyl, neopentyl, n-hexyl, isohexyl or n-heptyl, preferably ethyl and especially methyl.

Lower alkyl substituted by halogen is preferably trifluoromethyl.

Lower alkanoyl as such or in composed radicals such as lower alkanoyloxy etc. is e.g. formyl, acetyl, propionyl, n-butyryl, pivaloyl or valeroyl.

Halogen is preferably chloro or fluoro, but may also be bromo or iodo.

Phenylsulfonylamino means the radical —$NHSO_2C_6H_5$, lower alkylsulfonyl is —$SO_2$-lower alkyl.

Ureido and lower alkylureido represent the radicals —NH—$CONH_2$ and —NH—CONHAlk (3-alkylureido) or —NAlk-$CONH_2$ (1-alkylureido) respectively, wherein Alk is lower alkyl.

In lower alkoxy radicals which are substituted by hydroxy, epoxy, lower alkoxy, amino, lower alkylamino, di-lower alkylamino or halogen, the substituents mentioned are normally separated from the oxy group in lower alkoxy by at least two carbon atoms.

Suitable aryl groups include anthryl, phenanthryl, phenyl and naphthyl. Phenyl and naphthyl are preferred.

Heteroaryl groups may have up to 4 heteroatoms which may be the same or different selected from O, N and S. Suitable heteroaryl groups include benzofuranyl, pyrrolyl, imidazolyl, pyrazolyl, isothiazolyl, isoxazolyl, pyridyl, pyrazinyl, pyrimidinyl, pyridazinyl, indolizinyl, indazolyl, purinyl, quinolyl, naphthyridinyl, quinoxalinyl or phenoxazinyl.

Compounds of formula I are preferred in which $R^1$ is —$(CH_2)_m$— wherein m is 1, 2 or 3; or phenyl which is attached to the —$P(O)(OH)_2$ group via —$(CH_2)_n$— in the para-position of the phenyl ring, wherein n is 1 or 2; $R^2$ is $R^3R^4$ wherein $R^3$ is —$(CH_2)_p$— wherein p is zero, 1, 2 or 3, and $R^4$ is unsubstituted phenyl or naphthyl, or phenyl or naphthyl which is mono-, di- or tri-substituted by $C_{1-4}$-alkyl, halogen, cyano, nitro, phenoxy or benzoyl; and $X^-$ is $Cl^-$, $Br^-$, $ClO_4^-$ $PF_6^-$, $BF_4^-$, $C_2F_6NO_4S_2^-$ or $CF_3SO_3^-$, especially $Cl^-$ or $PF_6^-$.

Also preferred are compounds of formula I in which $R^1$ is phenyl which is attached to the —P(O)(OH)$_2$ group via —(CH$_2$)$_n$— in the para-position of the phenyl ring, wherein n is 1 or 2; $R^2$ is $R^3R^4$ wherein $R^3$ is —(CH$_2$)$_p$— wherein p is zero, 1, 2 or 3 and $R^4$ is —P(O)(OH)$_2$; and $X^-$ is $Cl^-$, $Br^-$, $ClO_4^-$ $PF_6^-$, $BF_4^-$, $C_2F_6NO_4S_2^-$ or $CF_3SO_3^-$, especially $Cl^-$ or $PF_6^-$.

Especially preferred are the following compounds of formula I:

(1) 1-Phosphonoethyl-1'-(3-propylphenyl)-4,4'-bipyridinium dichloride;
(2) 1-Phosphonoethyl-1'-(3-propylphenyl)-4,4'-bipyridinium bis-hexafluorophosphate;
(3) 1-Phosphonoethyl-1'-(2,4,6-trimethylphenyl)-4,4'-bipyridinium dichloride;
(4) 1-Phosphonoethyl-1'-(2,4,6-trimethylphenyl)-4,4'-bipyridinium bis-hexafluorophosphate;
(5) 1-Phosphonoethyl-1'-(naphthyl)-4,4'-bipyridinium dichloride;
(6) 1-Phosphonoethyl-1'-(4-cyanonaphthyl)-4,4'-bipyridinium dichloride;
(7) 1-Phosphonoethyl-1'-(4-methylphenyl)-4,4'-bipyridinium dichloride;
(8) 1-Phosphonoethyl-1'-(4-cyanophenyl)-4,4'-bipyridinium dichloride;
(9) 1-Phosphonoethyl-1'-(4-fluorophenyl)-4,4'-bipyridinium dichloride;
(10) 1-Phosphonoethyl-1'-(4-phenoxyphenyl)-4,4'-bipyridinium dichloride;
(11) 1-Phosphonoethyl-1'-(4-t-butylphenyl)-4,4'-bipyridinium dichloride;
(12) 1-Phosphonoethyl-1'-(2,6-dimethylphenyl)-4,4'-bipyridinium dichloride;
(13) 1-Phosphonoethyl-1'-(3,5-dimethylphenyl)-4,4'-bipyridinium dichloride;
(14) 1-Phosphonoethyl-1'-(4-benzophenone)-4,4'-bipyridinium dichloride;
(15) 1-Phosphonobenzyl-1'-(3-propylphenyl)-4,4'-bipyridinium dichloride;
(16) 1-Phosphonobenzyl-1'-(3-propylphenyl)-4,4'-bipyridinium bis-hexafluorophosphate;
(17) 1-Phosphonobenzyl-1'-(phosphonoethyl)-4,4'-bipyridinium dichloride;
(18) 1-Phosphonobenzyl-1'-(2,4-dinitrophenyl)-4,4'-bipyridinium dichloride;
(19) 1-Phosphonobenzyl-1'-(2,4-dinitrophenyl)-4,4'-bipyridinium bis-hexafluorophosphate;
(20) 1-Phosphonobenzyl-1'-(4-phenoxyphenyl)-4,4'-bipyridinium dichloride;
(21) 1-Phosphonobenzyl-1'-(4-phenoxyphenyl)-4,4'-bipyridinium bis-hexafluorophosphate;
(22) 1-Phosphonobenzyl-1'-(4-fluorophenyl)-4,4'-bipyridinium dichloride;
(23) 1-Phosphonobenzyl-1'-(4-methylphenyl)-4,4'-bipyridinium dichloride;
(24) 1-Phosphonobenzyl-1'-(2,4,6-trimethylphenyl)-4,4'-bipyridinium dichloride;
(25) 1-Phosphonobenzyl-1'-benzyl-4,4'-bipyridinium dichloride;
(26) 1-Phosphonobenzyl-1'-naphthyl-4,4'-bipyridinium dichloride;
(27) 1-Phosphonobenzyl-1'-phenyl-4,4'-bipyridinium dichloride;
(28) 1-Phosphonobenzyl-1'-(4-cyanophenyl)-4,4'-bipyridinium dichloride;
(29) 1-Phosphonobenzyl-1'-(4-benzophenone)-4,4'-bipyridinium dichloride;
(30) 1-Phosphonobenzyl-1'-(4-cyanonaphthyl)-4,4'-bipyridinium dichloride;
(31) 1-Phosphonobenzyl-1'-(2,6-dimethylphenyl)-4,4'-bipyridinium dichloride;
(32) 1-Phosphonobenzyl-1'-(3,5-dimethylphenyl)-4,4'-bipyridinium dichloride; and
(33) 1-Phosphonoethyl-1'-(2,4,6-trimethylphenyl)-4,4'-bipyridinium trifluoromethanesulfonimide.

Compounds of formula V are preferred in which each R is independently methyl or ethyl; $R^1$ is —(CH$_2$)$_m$— wherein m is 1, 2 or 3, or phenyl which is attached to the —P(O)(OH)$_2$ group via —(CH$_2$)$_n$— in the para-position of the phenyl ring, wherein n is 1 or 2; and each $X'^-$ is independently $Br^-$ or $Cl^-$.

A preferred compound of formula V is 1-diethylbenzylphosphonate-1'-(2,4-dinitrophenyl)-4,4'-bipyridinium dichloride.

The compounds of formula I may be prepared by (a) reacting bipyridine of the formula II

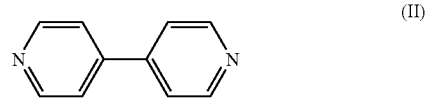

with 1-halo-2,4-dinitrobenzene, if appropriate, to form a compound of the formula III

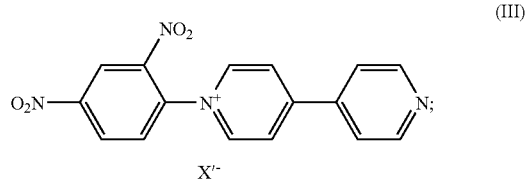

(b) reacting the compound of formula II or III with a phosphonylating agent of the formula $R^1$—Y—P(O)(OR)$_2$ to form a compound of the formula IV

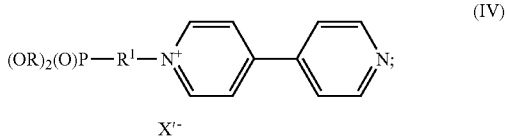

(c) reacting the compound of formula IV with 1-halo-2,4-dinitrobenzene, if appropriate, to form a compound of the formula V

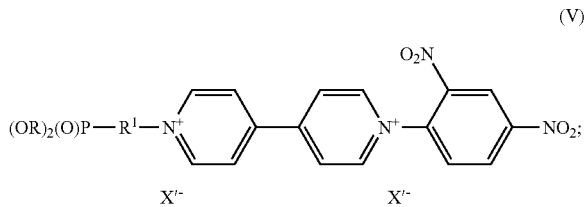

(V)

(d) reacting the compound of formula IV or V with a compound of the formula R²—Y to form a compound of the formula VI

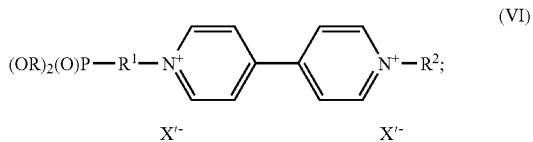

(VI)

(e) hydrolysing the compound of formula VI to form a compound of the formula I',

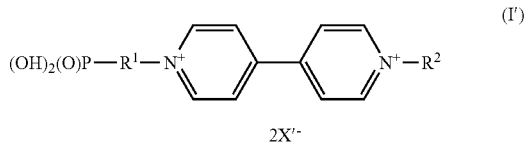

(I')

and if appropriate, (f) converting the compound of formula I' to a compound of the formula I

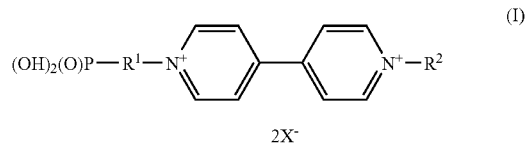

(I)

wherein in the above formulae each R is an ester forming group which may be the same or different, Y is halogen or amino, X'⁻ is halogen, preferably Br⁻ or Cl⁻, and R¹, R² and X⁻ are as already defined.

Step (a) of the above process is only carried out when compounds of the formula I are required wherein R¹ is other than —(CH₂)$_m$—; and step (c) is only carried out when R² in the formula I compounds is other than —(CH₂)$_p$— P(O)(OH)₂. The 1-halo-2,4-dinitrobenzene used in steps (a) and (c) is preferably 1-chloro-2,4-dinitrobenzene.

Phosphonylating agents used in step (b) are preferably dialkylhaloalkylphosphonates, such as diethylbromoethylphosphonate, and dialkyl-4-amino aryl or substituted aryl phosphonates, such as diethyl-4-aminobenzyl phosphonate or diethyl-4-aminonaphthyl phosphonate.

Suitable reagents of the formula R²—Y used in step (d) include haloalkylbenzenes, such as bromopropylbenzene, and aniline or substituted anilines.

The reactions steps (a)-(d) are generally carried out at refluxing temperature in a suitable solvent. Preferred solvents include toluene, acetonitrile and ethanol.

Hydrolysis step (e) is typically carried out in an solution of hydrochloric acid or hydrobromic acid.

Step (f) is carried out when a compound of formula I is required wherein X⁻ is other that Br⁻ or Cl⁻. The conversion of X'⁻ to X⁻ is effected by reacting a compound of formula I' with a salt of the desired balancing ion in aqueous solution. Conversion of X'⁻ to X⁻ can confer greater stability and greater solubility of the chromophore in a wider range of solvents, resulting in the use of less concentrated solutions in electrochromic devices with consequent reduction in costs.

The compounds of formula I improve the performance of electrochromic devices, in particular those comprising nano-structured films. The compounds of formula I can provide multiple colours, with enhanced stability for green colours, which has not previously been achieved.

The invention is illustrated in the following Examples.

EXAMPLE 1

Synthesis of 1-Phosphonoethyl-1'-(3-propylphenyl)-4,4'-bipyridinium dichloride (Compound 1)

(i) Synthesis of 1-Diethyl ethylphosphonate-4,4'-bipyridinium bromide 4,4'-Bipyridine (100 g, 0.64 moles) and diethyl bromoethylphosphonate (157 g, 0.64 moles) in toluene (500 ml) in a 1 L round bottomed flask was refluxed until the solid precipitate of the monocation salt was formed. The precipitate was filtered hot. The filtrate was refluxed again and the process repeated until no more solid formed. A yield of 95 g of the monocation was obtained.

(ii) Synthesis of 1-Diethyl ethylphosphonate-1'-(3-propylphenyl)-4,4'-bipyridinium dibromide 1-Diethyl ethylphosphonate-4,4'-bipyridinium bromide (0.005 moles) was added to 1-bromo-3-phenylpropane (0.075 moles) in acetonitrile (60 ml) and refluxed under stirring for twenty-four hours. The resulting precipitate was filtered, washed with hot acetonitrile and dried under vacuum to yield 1-diethyl ethylphosphonate-1'-(3-propylphenyl)-4,4'-bipyridinium dibromide.

(iii) Synthesis of 1-Phosphonoethyl-1'-(3-propylphenyl)-4,4'-bipyridinium dichloride 1-Diethyl ethylphosphonate-1'-(3-propylphenyl)-4,4'-bipyridinium dibromide was added to a 50% hydrochloric acid solution (60 ml) and allowed to reflux for twenty-four hours under stirring. The solvent was removed under vacuum and the compound was crystallised by the addition of ethanol, filtered and vacuum dried to yield 1-phosphonoethyl-1'-(3-propylphenyl)-4,4'-bipyridinium dichloride. This compound is purple in the reduced state.

$^1$H NMR (CD₃CN): δ 2.33-2.46(m, 4H), 2.81-2.83(m, 2H), 4.6-4.71(d, 2H), 4.74-4.93(m, 2H), 7.23-7.37(m, 5H), 8.44-9.3(m, 8H).

EXAMPLE 2

Synthesis of 1-Phosphonoethyl-1'-(3-propylphenyl)-4,4'-bipyridinium bis-hexafluorophosphate (Compound 2)

A solution of ammonium hexafluorophosphate (5 g) in water (20 ml) was added to a cold solution of 1-phosphonoethyl-1'-(3-propylphenyl)-4,4'-bipyridinium dichloride (2 g) prepared in Example 1 in water (20 ml). A precipitate of 1-phosphonoethyl-1'-(2,4,6-trimethylphenyl)-4,4'-bipyridinium bis-hexafluorophosphate (3 g) formed immediately and was filtered, washed with cold water and dried.

EXAMPLE 3

Synthesis of 1-Phosphonoethyl-1'-(2,4,6-trimethylphenyl)-4,4'-bipyridinium dichloride (Compound 3)

(i) Synthesis of 1-(Diethyl ethylphosphonate)-4,4'-bipyridinium bromide 4,4'-Bipyridine (100 g, 0.64 moles) and diethyl bromoethylphosphonate (157 g, 0.64 moles) in toluene (500 ml) in a 1 L round bottomed flask was refluxed until the solid precipitate of the monocation salt was formed. The precipitate was filtered hot. The filtrate was refluxed again and the process repeated until no more solid formed. A yield of 95 g of the monocation was obtained.

(ii) Synthesis of 1-Diethyl ethylphosphonate-1'-(2,4-dinitrophenyl)-4,4'-bipyridinium monobromide monochloride 1-Diethyl ethylphosphonate-4,4'-bipyridinium monobromide (50 g, 0.12 moles) was added to acetonitrile (400 ml) in a 1 L round-bottomed flask and refluxed for thirty minutes. The clear solution was decanted into a 1 L round-bottomed flask and 2,4-dinitrochlorobenzene (150 g, 0.74 moles) was added and refluxed for eighteen hours. The precipitate formed was filtered and digested with hot acetonitrile, filtered and dried under vacuum to yield 50 g of 1-diethyl ethylphosphonate-1'-(2,4-dinitrophenyl)-4,4'-bipyridinium monobromide monochloride.

(iii) Synthesis of the 1-diethyl ethylphosphonate-1'-(2,4,6-trimethylphenyl)-4,4'-bipyridinium monobromide monochloride 1-Diethyl ethylphosphonate-1'-(2,4-dinitrophenyl)-4,4'-bipyridinium monobromide monochloride (0.005 moles) was added to 2,4,6-trimethylaniline (0.075 moles) in ethanol (60 ml) and refluxed under stirring for 24 hrs. The ethanol was removed under vacuum and water (80 ml) was added. The suspension was stirred and filtered. The filtrate was decolourised with charcoal and the water was removed under vacuum. The resulting product was digested in acetonitrile, filtered and vacuum dried to yield the compound.

(iv) Synthesis of 1-phosphonoethyl-1'-(2,4,6-trimethylphenyl)-4,4'-bipyridinium dichloride 1-Diethyl ethylphosphonate-1'-(2,4,6-trimethylphenyl)-4,4'-bipyridinium monobromide monochloride was added to a 50% hydrochloric acid solution (60 ml) and refluxed for twenty four hours. The solvent was removed under vacuum and the compound was crystallised by the addition of ethanol, filtered and vacuum dried to yield the dichloride phosphonic acid derivative. This compound is blue in the reduced state.

$^1$H NMR (D$_2$O): δ 1.91(s, 6H), 2.24(s, 3H), 2.28-2.37(m, 2H), 4.76-4.85(m, 2H), 7.09(s, 2H), 8.46-9.1(m, 8H).

EXAMPLE 4

Synthesis of 1-phosphonoethyl-1'-(2,4,6-trimethylphenyl)-4,4'-bipyridinium bis-hexafluorophosphate (Compound 4)

A solution of ammonium hexafluorophosphate (4.3 g) in water (20 ml) was added to a solution of 1-phosphonoethyl-1'-(2,4,6-trimethylphenyl)-4,4'-bipyridinium dichloride (2 g) prepared in Example 3 in water (20 ml). A precipitate of 1-phosphonoethyl-1'-(2,4,6-trimethylphenyl)-4,4'-bipyridinium bis-hexafluorophosphate (2.5 g) formed immediately and was filtered and dried.

EXAMPLES 5-14

The procedure of Example 3 was repeated except that 2,4,6-trimethylaniline in step (iii) was replaced by the substituted aniline indicated in Table 1.

TABLE 1

| Example No./Compound No. | Compound Name/Colour in Reduced State | Substituted Aniline | $^1$H NMR |
|---|---|---|---|
| 5 | 1-Phosphonoethyl-1'-(naphthyl)-4,4'-bipyridinium dichloride (Green) | 1-Naphthylamine | (D$_2$O): δ 2.6-2.8(m, 2H), 4.8-4.95(m, 2H), 7.2-9.3(m, 15H). |
| 6 | 1-Phosphonoethyl-1'-(4-cyanonaphthyl)-4,4'-bipyridinium dichloride (Green) | 4-Amino-1-naphthalene-carbonitrile | (D$_2$O): δ 2.23-2.34(m, 2H), 4.69-4.82(m, 2H), 8.12-9.25(m, 14H). |
| 7 | 1-Phosphonoethyl-1'-(4-methylphenyl)-4,4'-bipyridinium dichloride (Green) | 4-Methylaniline | (D$_2$O): δ 2.32(s, 3H); 2.4-2.52(m, 2H); 4.75(m, 2H); 7.42(d, 2H); 7.53(d, 2H) 8.48-9.19(m, 8H). |
| 8 | 1-Phosphonoethyl-1'-(4-cyanophenyl)-4,4'-bipyridinium dichloride (Green) | 4-Cyanoaniline | (D$_2$O): δ 2.3(m, 2H), 4.8(m, 2H), 7.8(d, 2H), 8.16(d, 2H), 8.4-9.2(m, 8H). |
| 9 | 1-Phosphonoethyl-1'-(4-fluorophenyl)-4,4'-bipyridinium dichloride (Green) | 4-Fluoroaniline | (D$_2$O): δ 2.33(m, 2H), 4.81(m, 2H), 7.35(d, 2H), 7.71(d, 2H), 8.58-9.22(m, 8H). |
| 10 | 1-Phosphonoethyl-1'-(4-phenoxyphenyl)-4,4'-bipyridinium dichloride (Black) | 4-Phenoxyaniline | (CD$_3$CN, PF$_6$): δ 2.36(m, 2H), 4.88(m, 2H), 7.1-7.45(m, 5H), 7.44-7.74(m, 4H), 8.49-9.11(m, 8H). |
| 11 | 1-Phosphonoethyl-1'-(4-t-butylphenyl)-4,4'-bipyridinium dichloride (Green) | 4-tertButylaniline | (D$_2$O): δ1.29(s, 9H), 2.31(m, 2H), 4.78(m, 2H), 7.60(d, 2H,), 7.68(d, 2H), 8.56-9.2(m, 8H). |
| 12 | 1-Phosphonoethyl-1'-(2,6-dimethylphenyl)-4,4'-bipyridinium dichloride (Blue) | 2,6-Dimethylaniline | (D$_2$O): δ 2.03(s, 6H), 2.4-2.51(m, 2H), 4.88-4.98(m, 2H), 7.4-7.6(m, 3H), 8.6-9.2(m, 8H). |

TABLE 1-continued

| Example No./Compound No. | Compound Name/Colour in Reduced State | Substituted Aniline | $^1$H NMR |
|---|---|---|---|
| 13 | 1-Phosphonoethyl-1'-(3,5-dimethylphenyl)-4,4'-bipyridinium dichloride (Green) | 3,5-Dimethylaniline | ($D_2O$): δ 2.30(s, 6H), 2.35-2.43(m, 2H), 4.8(m, 2H), 7.28(s, 2H), 7.30(s, 1H), 8.4-9.16(m, 8H). |
| 14 | 1-Phosphonoethyl-1'-(4-benzophenone)-4,4'-bipyridinium dichloride (Green) | 4-Aminobenzophenone | ($D_2O$): δ, 2.32(m, 2H), 4.8(m, 2H), 7.4-8.2(m, 9H), 8.40-9.33(m, 8H). |

EXAMPLE 15

Synthesis of 1-Phosphonobenzyl-1'-(3-propylphenyl)-4,4'-bipyridinium chloride (Compound 15)

(i) Synthesis of 1-(2,4 Dinitrophenyl)-4,4'-bipyridinium chloride 4,4'-Bipyridine (10 g, 0.065 moles) and chloro-2,4-dinitrobenzene (13 g, 0.065 moles) in ethanol (150 ml) in a 250 ml flask were refluxed for fifteen hours and allowed to cool. The ethanol was removed under vacuum and acetone (200 ml) was added and the mixture was stirred. The suspension was filtered and dried under vacuum to yield 1-(2,4-dinitrophenyl)-4,4'-bipyridinium chloride (17.5 g).

(ii) Synthesis of 1-Diethyl benzylphosphonate-1'-bypyridinium chloride 1-(2,4-dinitrophenyl)-4,4'-bipyridinium chloride (7.3 g, 0.02 moles) and diethyl 4-aminobenzylphosphonate (5.5 g, 0.022 moles) in ethanol (150 ml) in a 250 ml flask were refluxed for six hours and allowed to cool. The ethanol was removed under vacuum and water (200 ml) was added and allowed to stir. The precipitate was filtered and the filtrate was decolourised with charcoal. The water was removed under vacuum to yield crude 1-diethyl benzylphosphonate-4,4'-bypyridinium chloride (8 g).

(iii) Synthesis of 1-Diethyl benzylphosphonate-1'-(3-propylphenyl)-4,4'-bipyridinium dichloride 1-diethyl benzylphosphonate-4,1'-bypyridinium chloride (5 g, 0.0095 moles) was added to acetonitrile (100 ml) in a 250 ml flask and refluxed for thirty minutes. The supernatant solution was decanted into a 250 ml flask and 1-bromo-3-phenylpropane (3.8 g, 0.018 moles) was added and refluxed for forty-eight hours. The precipitate formed was filtered and digested with hot acetonitrile, filtered and dried under vacuum to yield 1-diethyl benzylphosphonate-1'-(3-propylphenyl)-4,4'-bipyridinium dichloride (4 g).

(iv) Synthesis of 1-Phosphonobenzyl-1'-(3-propylphenyl)-4,4'-bipyridinium dichloride 1-Diethyl benzylphosphonate-1'-(3-propylphenyl)-bipyridinium dichloride (4 g) was added to a 50% Hydrochloric acid solution (60 ml) and allowed to reflux for twenty four hours under stirring. The solvent was removed under vacuum and the compound was crystallised by the addition of ethanol, filtered and vacuum dried to yield 1-phosphonobenzyl-1'-(3-propylphenyl)-4,4'-bipyridinium dichloride (3.2 g). This compound is green in the reduced state.

$^1$H NMR (CD$_3$CN): δ 2.4 (m, 4H), 2.8 (m, 2H), 3.35 (d, 2H), 4.8 (m, 2H), 7.22 (m, 5H), 8.6-9.4 (m, 8H).

EXAMPLE 16

Synthesis of 1-Phosphonobenzyl-1'-(3-propylphenyl)-4,4'-bipyridinium bis-hexafluorophosphate (Compound 16)

A solution of ammonium hexafluorophosphate (4 g) in water (20 ml) was added to a solution of 1-phosphonobenzyl-1'-(3-propylphenyl)-4,4'-bipyridinium dichloride (2 g) prepared in Example 15 in water (20 ml). A precipitate of 1-phosphonobenzyl-1'-(3-propylphenyl)-4,4'-bipyridinium bis-hexafluorophosphate (2.2 g) formed immediately and was filtered and dried.

EXAMPLE 17

Synthesis of 1-Phosphonobenzyl-1'-(phosphonoethyl)-4,4'-bipyridinium dichloride (Compound 17)

(i) Synthesis of 1-(2,4 Dinitrophenyl)-4,4'-bipyridinium chloride 4,4'-Bipyridine (10 g, 0.065 moles) and chloro-2,4-dinitrobenzene (13 g, 0.065 moles) in ethanol (150 ml) in a 250 ml flask were refluxed for fifteen hours and allowed to cool. The ethanol was removed under vacuum and acetone (200 ml) was added and the mixture was stirred. The suspension was filtered and dried under vacuum to yield 1-(2,4-dinitrophenyl)-4,4'-bipyridinium chloride (17.5 g).

(ii) Synthesis of 1-Diethyl benzylphosphonate-4,4'-bipyridinium chloride 1-(2,4-dinitrophenyl)-4,4'-bipyridinium chloride (7.3 g, 0.02 moles) and diethyl 4-aminobenzylphosphonate (5.5 g, 0.022 moles) in ethanol (150 ml) in a 250 ml flask were refluxed for six hours and allowed to cool. The ethanol was removed under vacuum and water (200 ml) was added and allowed to stir. The precipitate was filtered and the filtrate was decolourised with charcoal. The water was removed under vacuum to yield crude 1-diethyl benzylphosphonate-4,4'-bipyridinium chloride (8 g)

(iii) Synthesis of 1-Diethyl benzylphosphonate-1'-diethyl ethylphosphonate-4,4'-bipyridinium dichloride 1-diethyl benzylphosphonate-4,4'-bypyridinium chloride (5 g, 0.013 moles) was added to acetonitrile (100 ml) in a 250 ml flask and refluxed for thirty minutes. The supernatant solution was decanted into a 250 ml flask and diethyl bromoethylphosphonate (6.3 g, 0.026 moles) was added and refluxed for forty-eight hours. The precipitate formed was filtered and digested with hot acetonitrile, filtered and dried under vacuum to yield 1-diethyl benzylphosphonate-1'-diethyl ethylphosphonate-4,4'-bipyridinium dichloride (8 g).

(iv) Synthesis of 1-Phosphonobenzyl-1'-phosphonoethyl-4,4'-bipyridinium dichloride 1-Diethyl benzylphosphonate-1'-diethyl ethylphosphonate-4,4'-bipyridinium dichloride (5 g) was added to a 50% Hydrochloric acid solution (60 ml) and allowed to reflux for twenty-four hours under stirring. The solvent was removed under vacuum and the compound was crystallised by the addition of ethanol, filtered and vacuum dried to yield 1-phosphonobenzyl-1'-phosphonoethyl-4,4'-bipyridinium dichloride (3.6 g). This compound is green in the reduced state.

$^1$H NMR (D$_2$O): δ 2.4 (m, 2H), 3.32 (d, 2H), 4.85 (m, 2H), 7.8 (m, 4H), 8.6-9.2 (m, 8H).

EXAMPLE 18

Synthesis of 1-Phosphonobenzyl-1'-(2,4-dinitrophenyl)-4,4'-bipyridinium dichloride (Compound 18)

(i) Synthesis of 1-(2,4 Dinitrophenyl)-4,4'-bipyridinium chloride 4,4'-Bipyridine (10 g, 0.065 moles) and chloro-2,4-dinitrobenzene (13 g, 0.065 moles) in ethanol (150 ml) in a 250 ml flask were refluxed for fifteen hours and allowed to cool. The ethanol was removed under vacuum and acetone (200 ml) was added and the mixture was stirred. The suspension was filtered and dried under vacuum to yield 1-(2,4-dinitrophenyl)-4,4'-bipyridinium chloride (17.5 g).

(ii) Synthesis of 1-Diethyl benzylphosphonate-4,4'-bypyridinium chloride 1-(2,4-dinitrophenyl)-4,4'-bipyridinium chloride (7.3 g, 0.02 moles) and diethyl 4-aminobenzylphosphonate (5.5 g, 0.022 moles) in ethanol (150 ml) in a 250 ml flask were refluxed for six hours and allowed to cool. The ethanol was removed under vacuum and water (200 ml) was added and allowed to stir. The precipitate was filtered and the filtrate was decolourised with charcoal. The water was removed under vacuum to yield crude 1-diethyl benzylphosphonate-4,4'-bypyridinium chloride (8 g).

(iii) Synthesis of 1-Diethyl benzylphosphonate-1'-(2,4-dinitrophenyl)-bipyridinium dichloride 1-diethyl benzylphosphonate-4,4'-bypyridinium chloride (5 g, 0.013 moles) was added to acetonitrile (100 ml) in a 250 ml flask and refluxed for thirty minutes. The supernatant solution was decanted into a 250 ml flask and 2,4-dinitrochlorobenzene (10 g, 0.05 moles) was added and refluxed for forty-eight hours. The precipitate formed was filtered and digested with hot acetonitrile, filtered and dried under vacuum to yield 1-diethyl benzylphosphonate-1'-(2,4-dinitrophenyl)-4,4'-bipyridinium dichloride (6 g).

$^1$H NMR (D$_2$O): δ 1.15 (6H), 3.42 (2H), 4.02 (4H), 7.57 (1H), 7.71 (1H), 8.18 (1H), 8.78 (4H), 9.31 (4H)

(iv) Synthesis of 1-Phosphonobenzyl-1'-(2,4-dinitrophenyl)-4,4'-bipyridinium dichloride 1-Diethyl benzylphosphonate-1'-(2,4-dinitrophenyl)-4,4'-bipyridinium dichloride (5 g) was added to a 50% Hydrochloric acid solution (60 ml) and allowed to reflux for twenty-four hours under stirring. The solvent was removed under vacuum and the compound was crystallised by the addition of ethanol, filtered and vacuum dried to yield 1-phosphonobenzyl-1'-(2,4-dinitrophenyl)-4,4'-bipyridinium dichloride (3.8 g). This compound is green in the reduced state.

$^1$H NMR (D$_2$O): δ 2.45 (m, 2H), 4.85 (m, 2H), 8.2 (m, 2H), 8.45 (d, 1H), 8.8-9.4 (m, 8H).

EXAMPLE 19

Synthesis of 1-Phosphonobenzyl-1'-(2,4-dinitrophenyl)-4,4'-bipyridinium bis-hexafluorophosphate (Compound 19)

A solution of ammonium hexafluorophosphate (4 g) in water (20 ml) was added to a solution of 1-phosphonobenzyl-1'-(2,4-dinitrophenyl)-4,4'-bipyridinium dichloride (2 g) prepared in Example 18 in water (20 ml). A precipitate of 1-phosphonobenzyl-1'-(2,4-dinitrophenyl)-4,4'-bipyridinium bis-hexafluorophosphate (2.8 g) formed immediately and was filtered and dried.

EXAMPLE 20

Synthesis of 1-Phosphonobenzyl-1'-(4-phenoxyphenyl)-4,4'-bipyridinium dichloride (Compound 20)

(i) Synthesis of 1-(2,4 Dinitrophenyl)-4,4'-bipyridinium chloride 4,4'-Bipyridine (10 g, 0.065 moles) and chloro-2,4-dinitrobenzene (13 g, 0.065 moles) in ethanol (150 ml) in a 250 ml flask were refluxed for fifteen hours and allowed to cool. The ethanol was removed under vacuum and acetone (200 ml) was added and the mixture was stirred. The suspension was filtered and dried under vacuum to yield 1-(2,4-dinitrophenyl)-4,4'-bipyridinium chloride (17.5 g).

(ii) Synthesis of 1-Diethyl benzylphosphonate-4,4'-bypyridinium chloride 1-(2,4-dinitrophenyl)-4,4'-bipyridinium chloride (7.3 g, 0.02 moles) and diethyl 4-aminobenzylphosphonate (5.5 g, 0.022 moles) in ethanol (150 ml) in a 250 ml flask were refluxed for six hours and allowed to cool. The ethanol was removed under vacuum and water (200 ml) was added and allowed to stir. The precipitate was filtered and the filtrate was decolourised with charcoal. The water was removed under vacuum to yield crude 1-diethyl benzylphosphonate-4,4'-bypyridinium chloride (8 g).

(iii) Synthesis of 1-Diethyl benzylphosphonate-1'-(2,4-dinitrophenyl)-4,4'-bipyridinium dichloride 1-diethyl benzylphosphonate-4,4'-bypyridinium chloride (5 g, 0.013 moles) was added to acetonitrile (100 ml) in a 250 ml flask and refluxed for thirty minutes. The supernatant solution was decanted into a 250 ml flask and 2,4-dinitrochlorobenzene (10 g, 0.05 moles) was added and refluxed for forty-eight hours. The precipitate formed was filtered and digested with hot acetonitrile, filtered and dried under vacuum to yield 1-diethyl benzylphosphonate-1'-(2,4-dinitrophenyl)-4,4'-bipyridinium dichloride (6 g).

(iv) Synthesis of 1-Diethyl benzylphosphonate-1'-(4-phenoxyphenyl)-4,4'-bipyridinium dichloride 1-Diethyl benzylphosphonate-1'-(2,4-dinitrophenyl)-bipyridinium dichloride (3 g, 0.005 moles) and 4-phenoxyaniline (1 g, 0.0055 moles) were refluxed together in ethanol (60 ml) for twenty four hours. The ethanol was removed under vacuum and water (80 ml) was added. The suspension was stirred and filtered. The filtrate was decolourised with charcoal and the water was removed under vacuum. The crude product was digested in acetonitrile, filtered and vacuum dried to yield 1-diethyl benzylphosphonate-1'-(4-phenoxyphenyl)-4,4'-bipyridinium dichloride (2 g)

(v) Synthesis of 1-Phosphonobenzyl-1'-(4-phenoxyphenyl)-4,4'-bipyridinium dichloride 1-Diethyl benzylphosphonate-1'-(4-phenoxyphenyl)-bipyridinium dichloride (2 g) was added to a 50% Hydrochloric acid solution (60 ml) and allowed to reflux for twenty four hours under stirring. The solvent was removed under vacuum and the compound was crystallised by the addition of ethanol, filtered and vacuum dried to yield 1-phosphonobenzyl-1'-(4-phenoxyphenyl)-4,4'-bipyridinium dichloride (1.6 g).
$^1$H NMR (D$_2$O, dichloride): δ 3.16(d, 2H), 6.95-7.8(m, 13H), 8.6-9.2(m, 8H).

EXAMPLE 21

Synthesis of 1-Phosphonobenzyl-1'-(4-phenoxyphenyl)-4,4'-bipyridinium bis-hexafluorophosphate (Compound 21)

A solution of ammonium hexafluorophosphate (2 g) in water (20 ml) was added to a solution of 1-phosphonobenzyl-1'-(4-phenoxyphenyl)-4,4'-bipyridinium di-chloride (1 g) prepared in Example 20 in water (20 ml). A precipitate of 1-phosphonobenzyl-1'-(4-phenoxy-phenyl)-4,4'-bipyridinium bis-hexafluorophosphate (1.4 g) formed immediately and was filtered and dried.

EXAMPLES 22-24

The procedure of Example 20 was repeated except that the 4-phenoxyaniline in step (iv) was replaced by the substituted aniline indicated in Table 2.

TABLE 2

| Example No./Compound No. | Compound Name/Colour in Reduced State | Substituted Aniline | $^1$H NMR |
|---|---|---|---|
| 22 | 1-Phosphonobenzyl-1'-(4-fluorophenyl)-4,4'-bipyridinium dichloride (Green) | 4-Fluoroaniline | (D$_2$O, dichloride): δ 3.15(d, 2H), 7.1-7.7(m, 8H), 8.6-9.3(m, 8H) |
| 23 | 1-Phosphonobenzyl-1'-(4-methylphenyl)-4,4'-bipyridinium dichloride (Green) | 4-Methylaniline | (D$_2$O, dichloride): δ 2.33(s, 3H), 3.25(d, 2H), 7.35-7.8(m, 8H), 8.7-9.3(m, 8H) |
| 24 | 1-Phosphonobenzyl-1'-(2,4,6-trimethyl-phenyl)-4,4'-bipyridinium dichloride (Blue) | 2,4,6-Trimethylaniline | (D$_2$O, dichloride): δ 1.99(s, 9H), 3.18(d, 2H), 7.12(s, 2H), 7.5-7.7(dd, 4H), 8.6-9.3(m, 8H) |

EXAMPLE 25

A fluorine doped tin oxide (FTO, 15 Ω per square) coated glass substrate (20 mm×10 mm) was coated with nanocrystalline titanium dioxide (20 mm×10 mm) by screenprinting. The coating was heated in air at 450° C. for 45 minutes to give a transparent nanostructured titanium dioxide film.

The film was immersed in a solution of Compound 3, prepared in Example 3, i.e. 1-phosphonoethyl-1'-(2,4,6-trimethylphenyl)-4,4'-bipyridinium dichloride (0.001M), in deionised water for 30 minutes. In this way the chromophore was adsorbed to the nanostructured film. The film was rinsed in ethanol for 15 minutes and air-dried. An electrochemical cell was assembled using the prepared film as the cathode. A silver/silver chloride electrode was used as the reference electrode and a platinum wire as the counter electrode. The three electrodes were immersed in a 0.2M electrolyte solution of lithium perchlorate in gamma butyrolactone that was purged with nitrogen.

The electrodes were connected to a Solartron 1285 potentostat and a voltage sweep was performed from +0.5V to −1.1V at a scan rate of 50 mV/s. The cathodic reduction of the adsorbed Compound 3 resulted in a blue colouration of the device. As the voltage sweep continued and Compound 3 was oxidised, the decolouration of Compound 3 was observed.

Electrodes comprising the compounds of Examples 5-14 were prepared and tested according to the above procedure, and the colour of each of the compounds in the reduced state is given in Table 1.

EXAMPLE 26

Cathodic electrodes comprising the compounds of Examples 3 and 17 were prepared as in Example 25. These electrodes were sealed to a second FTO (15 Ω/square) coated glass substrate with an epoxy glue and heated to 130° C. for 1 hour to cure the glue. The cells thus formed were filled under vacuum with an electrolyte solution containing ferrocene (0.05M) and lithium perchlorate (0.2M) in gamma butyrolactone and finally sealed with a UV curable glue. Application of −1.3V across the resulting electrochromic devices lead to uniform colouration and upon removal of the voltage the devices returned to their clear state. UV\Vis spectral measurements were made on a Shimadzu UV2401PC spectrometer and transmission levels are reported at 550 nm.

The data obtained are shown in Table 3 and indicate a successful functioning of each device in that there is a significant reduction in transmission in switching from the clear to the coloured state.

TABLE 3

| Device No. | Compound of Example No. | Transmission in Clear State | Transmission in Coloured State |
|---|---|---|---|
| 1 | 3 | 72% | 31% |
| 2 | 17 | 75% | 46% |

EXAMPLE 27

A cathodic electrode was prepared as in Example 25 with the exception that the film was immersed in an equimolar (0.001M) solution of two viologens, 1-phosphonoethyl-1'-(2,4,6-trimethylphenyl)-4,4'-bipyridinium dichloride (Compound 3 prepared in Example 3) and 1-phosphonobenzyl-1'-(phosphonoethyl)-4,4'-bipyridinium dichloride (Compound 17 prepared in Example 17). The cathode was sealed to a second substrate, filled and finally sealed according to Example 26.

Application of −1.3V across the resulting electrochromic device lead to a uniform green/grey colouration and upon removal of the voltage the device returned to its clear state. UV/Vis spectral measurements were carried out as described in Example 26.

It can be observed that this device functions similarly to those in Example 26. However, the colouration is different when two viologens are used (i.e. green/grey) as compared with the previous devices which only have one viologen.

TABLE 4

| Device No. | Compound of Example No. | Transmission (Clear State) | Transmission in Coloured State |
|---|---|---|---|
| 1 | 3 + 17 | 82% | 25% |

EXAMPLE 28

Cathodic electrodes comprising the compounds of Examples 3, 7, 9, 10, 11, 13 and 17 were prepared as in Example 25. Anodes were constructed from respective second FTO substrates (50 mm×50 mm). These substrates were coated with antimony doped tin oxide (ATO) by screenprinting and heated at 60° C. for 20-30 minutes. A white reflector paste comprising silica-coated titanium dioxide was applied by screenprinting over each ATO layer and each double layer was allowed to sinter at 450° C. for 45 minutes. Each set of two electrodes was bonded together in a sandwich configuration to form a cell. Each cell was filled with an electrolyte solution of lithium trifluormethanesulfonimide (10 mM) in gamma butyrolactone. The resulting devices were sealed and initial reflectance measurements were made on an Ocean Optics SD2000 spectrometer equipped with an integrating sphere.

Each device had a diffuse reflectance in the clear state of 36%. When a voltage of −1.3V was applied across each device, it coloured and the reflectance value at 550 nm dropped to approximately 2.5%. The ratio of the clear state reflectance to the coloured state reflectance is a measure referred to as the contrast ratio (CR). In each case, the contrast ratio was 36/2.5=14.4.

The stability of the devices prepared above was tested by cycling them between the coloured and clear states many thousands of times at a temperature of about 70° C. The contrast ratio (CR) was measured before and after cycling to assess the level of degradation of the devices. The results are shown in Table 5.

TABLE 5

| Device No. | Compound No. | Number of Cycles | CR before | CR after |
|---|---|---|---|---|
| 1 | 3 | 1,000,000 | 14.4 | 13 |
| 2 | 7 | 50,000 | 14.4 | 14.4 |
| 3 | 9 | 50,000 | 14.4 | 14.4 |
| 4 | 10 | 50,000 | 14.4 | 14.4 |
| 5 | 11 | 50,000 | 14.4 | 14 |
| 6 | 13 | 50,000 | 14.4 | 14 |
| 7 | 17 | 200,000 | 14.4 | 14.4 |

The results show that degradation of the contrast ratio is negligible even at $1 \times 10^6$ cycles.

The invention claimed is:

1. An electrode or an electrochromic device comprising a compound according to formula I:

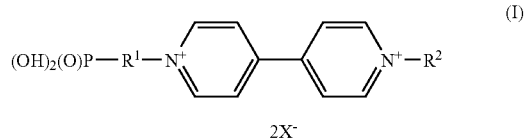

wherein $R^1$ is —$(CH_2)_m$— wherein m is zero or an integer from 1 to 10;

and $R^2$ is $R^3R^4$ wherein $R^3$ is —$(CH_2)_p$— wherein p is zero or an integer from 2 to 10; and $R^4$ is (a) unsubstituted phenyl or naphthyl, or phenyl or naphthyl which is mono-, di- or tri-substituted by $C_{1-4}$-alkyl, halogen, cyano, phenoxy or benzoyl (b) or branched-chain alkyl or alkenyl, or cycloalkyl, each having up to 10 carbon atoms, and $X^-$ is a charge-balancing ion; with the proviso that $R_1$ cannot be —$(CH_2)_m$ wherein m is 2, when $R^2$ is phenyl.

2. An electrode or an electrochromic device comprising a compound according to formula V

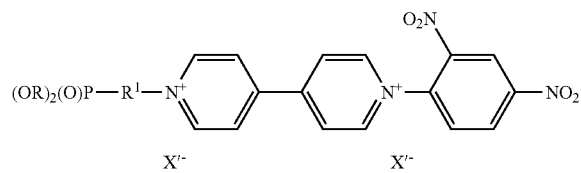

wherein $R^1$ is —$(CH_2)_m$— wherein m is zero or an integer from 1 to 10; each R is an ester forming group which may be the same or different, and each $X'^-$ is independently halogen.

* * * * *